(12) United States Patent
Brock-Fisher

(10) Patent No.: US 6,612,989 B1
(45) Date of Patent: Sep. 2, 2003

(54) SYSTEM AND METHOD FOR SYNCHRONIZED PERSISTENCE WITH CONTRAST AGENT IMAGING

(75) Inventor: George Brock-Fisher, Andover, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/174,282

(22) Filed: Jun. 18, 2002

(51) Int. Cl.[7] ................................................. A61B 8/00
(52) U.S. Cl. ...................................................... 600/447
(58) Field of Search ................................ 600/437, 441, 600/442, 443, 447, 449, 454, 455, 456

(56) References Cited

U.S. PATENT DOCUMENTS

| 5,410,516 A | 4/1995 | Uhlendorf et al. |
| 5,577,505 A | 11/1996 | Brock-Fisher et al. |
| 5,788,635 A | 8/1998 | Wright et al. |
| 5,971,928 A * | 10/1999 | Dodd et al. ................. 600/458 |
| 6,083,168 A * | 7/2000 | Hossack et al. ............. 600/443 |
| 6,322,505 B1 * | 11/2001 | Hossack et al. ............. 600/437 |
| 6,352,511 B1 * | 3/2002 | Hossack et al. ............. 600/443 |

* cited by examiner

Primary Examiner—Francis J. Jaworski
Assistant Examiner—Maulin Patel
(74) Attorney, Agent, or Firm—John Vodopia (57) ABSTRACT

A system and method for synchronized persistence with ultrasonic harmonic imaging of both tissue and tissue perfused with a contrast agent are disclosed. The ultrasonic harmonic imaging system comprises a frame memory, a frame processor, a persistence actuator, and a persistence controller. In a preferred embodiment, the persistence actuator disables persistence filtering in response to contrast agent destructive ultrasonic transmissions. A method for observing an ultrasonic response of a contrast agent may be performed by: introducing a contrast agent into tissue targeted for imaging; insonifying the tissue with a first ultrasound transmit signal suited to observe the contrast agent and the tissue; modifying a transmit signal parameter to destroy a substantial portion of the contrast agent; disabling persistence filtering while the modified transmit signal is actuated; and enabling persistence filtering while observing the re-perfusion of the tissue.

25 Claims, 9 Drawing Sheets

SYSTEM AND METHOD FOR SYNCHRONIZED PERSISTENCE WITH CONTRAST AGENT IMAGING

BACKGROUND OF THE INVENTION

1. Field of the Invention

The present disclosure relates to ultrasonic imaging. More particularly, the invention relates to a system and method that improves contrast agent imaging diagnostic evaluations.

2. Discussion of the Related Art

Harmonic Imaging of Tissue

Ultrasonic imaging has quickly replaced conventional X-rays in many clinical applications because of its image quality, safety, and low cost. Ultrasonic images are typically formed through the use of phased or linear array transducers which are capable of transmitting and receiving pressure waves directed into a medium such as the human body. Such transducers normally comprise multi-element piezoelectric materials, which vibrate in response to an applied voltage to produce the desired pressure waves. Piezoelectric transducer elements are typically constructed of lead zirconate titanate (PZT), with a plurality of elements being arranged to form a transducer assembly. A new generation ultrasonic transducer known as a micro-machined ultrasonic transducer (MUT) is also available. MUTs are typically fabricated using semiconductor-manufacturing techniques with a number of elements typically formed on a common substrate to form a transducer assembly. Regardless of the type of transducer element, the transducer elements may be further assembled into a housing possibly containing control electronics, the combination of which forms an ultrasonic probe. The ultrasonic probe may include acoustic matching layers between the surface of the various types of elements and the probe body. Ultrasonic probes may then be used along with an ultrasonic transceiver to transmit and receive ultrasonic pressure waves through the various tissues of the body. The various ultrasonic responses may be further processed by an ultrasonic imaging system to display the various structures and tissues of the body.

To obtain high quality images, the ultrasonic probe must be constructed so as to produce specified frequencies of pressure waves. Generally speaking, low frequency pressure waves provide deep penetration into the medium (e.g., the body), but produce poor resolution images due to the length of the transmitted wavelengths. On the other hand, high frequency pressure waves provide high resolution, but with poor penetration. Accordingly, the selection of a transmitting frequency has involved balancing resolution and penetration concerns. Unfortunately, resolution has suffered at the expense of deeper penetration and vice versa. Traditionally, the frequency selection problem has been addressed by selecting the highest imaging frequency (i.e., best resolution) which offers adequate penetration for a given application. For example, in adult cardiac imaging, frequencies in the 2 MHz to 3 MHz range are typically selected in order to penetrate the chest wall. Lower frequencies have not been used due to the lack of sufficient image resolution. Higher frequencies are often used for radiology and vascular applications where fine resolution is required to image small lesions and arteries affected by stenotic obstructions.

Recently, new methods have been studied in an effort to obtain both high resolution and deep penetration. One such method is known as harmonic imaging. Harmonic imaging is grounded on the phenomenon that objects, such as human tissues, develop and return their own non-fundamental frequencies, i.e., harmonics of the fundamental frequency. This phenomenon and increased image processing capabilities of digital technology, make it is possible to excite an object to be imaged by transmitting at a low (and therefore deeply penetrating) fundamental frequency ($f_o$) and receiving reflections at a higher frequency harmonic (e.g., $2f_o$) to form a high resolution image of an object. By way of example, a wave having a frequency less than 2 MHz can be transmitted into the human body and one or more harmonic waves having frequencies greater than 3 MHz can be received to form the image. By imaging in this manner, deep penetration can be achieved without a concomitant loss of image resolution.

However, in order to achieve the benefits of transmitting at a lower frequency for tissue penetration and receiving a harmonic frequency for improved imaging resolution, broadband transducers are required which can transmit sufficient bandwidth about the fundamental frequency and receive sufficient bandwidth about the harmonic(s). The s4 transducer available with the SONOS™ 5500 an ultrasound imaging system manufactured by and commercially available from Agilent Technologies, U.S.A., has a suitable bandwidth to achieve harmonic imaging with a single transducer thus providing a significant clinical improvement. Furthermore, the combination of the s4 transducer and the SONOS™ 5500 provide multiple imaging parameter choices using a single transducer, thus providing a penetration choice as well as a resolution choice.

Conventional ultrasound scanners can create two-dimensional B-mode images of tissue in which the brightness of a pixel is based on the intensity of the received ultrasonic echoes. In color flow imaging, the flow of blood or movement of tissue can be imaged. Measurement of blood flow in the heart and vessels using the Doppler effect is well known. The frequency shift of backscattered ultrasound waves may be used to measure the velocity of the backscatterers from tissues or blood. The frequency of sound waves reflecting from the inside of blood vessels, heart cavities, etc. is shifted in proportion to the velocity of the blood cells. The frequency of ultrasonic waves reflected from cells moving towards the transducer is positively shifted. Conversely, the frequency of ultrasonic reflections from cells moving away from the transducer is negatively shifted. The Doppler shift may be displayed using different colors to represent speed and direction of flow. In order to assist diagnosticians and operators the color flow image may be superimposed on the B-mode image.

Persistence Processing

Ultrasound images, like other images are subject to noise which may adversely affect the intensity values associated with the various pixels used to recreate the object or objects being observed. Ultrasound images, like some other images, also suffer from the effects of temporal noise in real-time image sequences. Conventional ultrasound imaging systems normally have an image frame filtering function, which acts on data in either polar or Cartesian coordinate formats.

One method for reducing temporal noise from an image is to use a filter which weights and sums corresponding pixel intensity values from the previous frame with a present input frame to generate a display pixel intensity. This is sometimes called "temporal filtering" or "persistence filtering." In this method, a previous display frame's pixel may be averaged with an input frame's pixel, using a weighting value α. The weighting value applies an equal degree of temporal filtering to all pixels in the frame. As a result, the method is data independent, i.e., not adaptive to changes in the underlying image data. While temporal noise is reduced, this simple filtering has the untoward effect of blurring or degrading small structures, the border of structures, or the borders of structures moving in the image field.

As will be further described below, continuous persistence filtering may be inappropriate when used in association with real-time imaging and high-power ultrasonic transmit pulses.

Contrast Imaging

Harmonic imaging can also be particularly effective when used in conjunction with contrast agents. In contrast agent imaging, gas or fluid filled micro-sphere contrast agents known as microbubbles are typically injected into a medium, normally the bloodstream. Because of their strong nonlinear response characteristics when insonified at particular frequencies, contrast agent resonation can be easily detected by an ultrasound transducer. By using harmonic imaging after introducing contrast agents, medical personnel can significantly enhance imaging capability for diagnosing the health of blood-filled tissues and blood flow dynamics within a patient's circulatory system. For example, contrast agent harmonic imaging is especially effective in detecting myocardial boundaries, assessing microvascular blood flow, and detecting myocardial perfusion.

The power or mechanical index of the incident ultrasonic pressure wave directly affects the contrast agent acoustical response. At lower powers, microbubbles formed by encapsulating one or more gaseous contrast agents with a material forming a shell thereon resonate and emit harmonics of the transmitted frequency. The magnitude of these microbubble harmonics depends on the magnitude of the excitation signal pulse. At higher acoustical powers, microbubbles rupture and emit strong broadband signals. In order to take advantage of these strong backscattered signals for imaging purposes, it is desired to have uniform destruction within the imaging plane. In general, the higher the transmitted frequency, the greater the variation in the response from the microbubble within the imaging plane. It has been determined that lower frequencies are more efficient at bubble destruction than higher frequencies.

Today's systems, in order to deal with the lack of uniformity in bubble detection and bubble destruction, use multi-pulse techniques to increase the signal-to-noise ratio and to increase destruction of microbubbles. However, multi-pulse techniques for detection of contrast agents require the user to be able to discriminate motion artifacts from true bubble resonance and destruction signals. For example, in high mechanical index (MI) triggered techniques, such as Harmonic Power Doppler, it is critical that triggering occurs during that portion of the cardiac cycle when the heart is relatively stationary. Discriminating between motion artifacts resulting from triggering and variations in the cardiac cycle has made diagnosis difficult for users and has slowed acceptance of contrast imaging in clinical practices.

U.S. Pat. No. 5,410,516 to Uhlendorf et al. discloses contrast agent imaging along with single pulse excitation techniques such as harmonic imaging. Specifically, Uhlendorf teaches that by choosing a radio frequency (RF) filter to selectively observe any integer harmonic (2nd, 3rd, etc.), subharmonic (e.g., 1/2 harmonic) or ultraharmonic (e.g., 3/2 harmonic) it is possible to improve the microbubble to tissue ratio. The second harmonic has proven most useful due to the large bubble response at this frequency as compared to higher order integer harmonics, subharmonics or ultraharmonics. The second harmonic also is most practical due to bandwidth limitations on the transducer (i.e., <70% bandwidth, where percent bandwidth is defined as the difference of the high corner frequency −6 dB point from the low corner frequency −6 dB point, divided by the center frequency.) However, single pulse excitation techniques together with harmonic imaging suffer from poor microbubble-to-tissue ratios as large tissue integer-harmonic signals mask the signal generated by the contrast agent.

Currently in the field of ultrasound contrast exams, it is customary to use a low-acoustic power imaging technique to image ultrasound contrast agents in real-time. While this imaging is performed, a sequence of several high-power transmit pulses are directed into the tissue of interest for the purpose of destroying or modifying the contrast agent in the field of view. Under appropriate conditions, contrast agent backscatterers may be substantially removed from a region of interest. This methodology permits an operator to observe and record the re-perfusion of contrast agent within various tissues of interest.

Before the advent of contrast imaging and as described previously, the technique of applying persistence or temporal filtering to video images has been used to improve the appearance of the image by reducing the effects of thermal noise by averaging. However, when applying the persistence filtering technique to a contrast agent enhanced ultrasonic image where a destructive transmit sequence is applied, the brighter frames of the destructive sequence are averaged by the persistence technique, thereby obscuring several of the resulting image frames containing the re-perfusion of the tissue under observation.

SUMMARY OF THE INVENTION

In response to these and other shortcomings of the prior art, the present invention relates to an improved ultrasonic imaging system and method for harmonic imaging of contrast agent perfused tissues. Briefly described, in architecture, the system can be implemented with a transducer, an ultrasonic imaging system, a video processor having a persistence module, a patient interface, and a diagnostics processor.

The present invention can also be viewed as providing a method for synchronized persistence with contrast agent destruction and re-perfusion imaging. In this regard, the method can be broadly summarized by the following steps: introducing at least one contrast agent; insonifying tissue with an ultrasound signal suited to permit real-time observation of an organ of interest; modifying one or more parameters associated with the transmit signal to generate a contrast agent destruction sequence; synchronizing the persistence circuits in the ultrasound system with the destruction sequence so that image frames during the destruction sequence do not contribute to persistence filtered results. This allows the persistence filtering to be applied during the subsequent re-perfusion of the contrast agent in the tissues of interest without the adverse residual affects from a high-power ultrasonic reflection during contrast agent destruction.

Other systems, methods, features, and advantages of the present invention will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Having summarized various aspects of the present invention, reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims. Turning now to the drawings, wherein like referenced numerals designate corresponding parts throughout the drawings, reference is made to FIG. 1, which illustrates a block diagram of an ultrasound imaging system capable of viewing tissue and contrast agents by varying the ultrasound transmit waveforms. An example of an ultrasonic imaging system capable of producing a series of ultrasonic pulses with multiple excitation levels is disclosed in U.S. Pat. No. 5,577,505 which shares a common assignee with the present application and the contents of which are incorporated herein in their entirety. An example of an ultrasound imaging system with increased sensitivity to non-linear contrast agent responses is disclosed in U.S. patent application Ser. No. 09/618,510, filed on Jul. 14, 2000, which shares a common assignee with the present application and the contents of which are also incorporated herein in their entirety.

Figure 1:
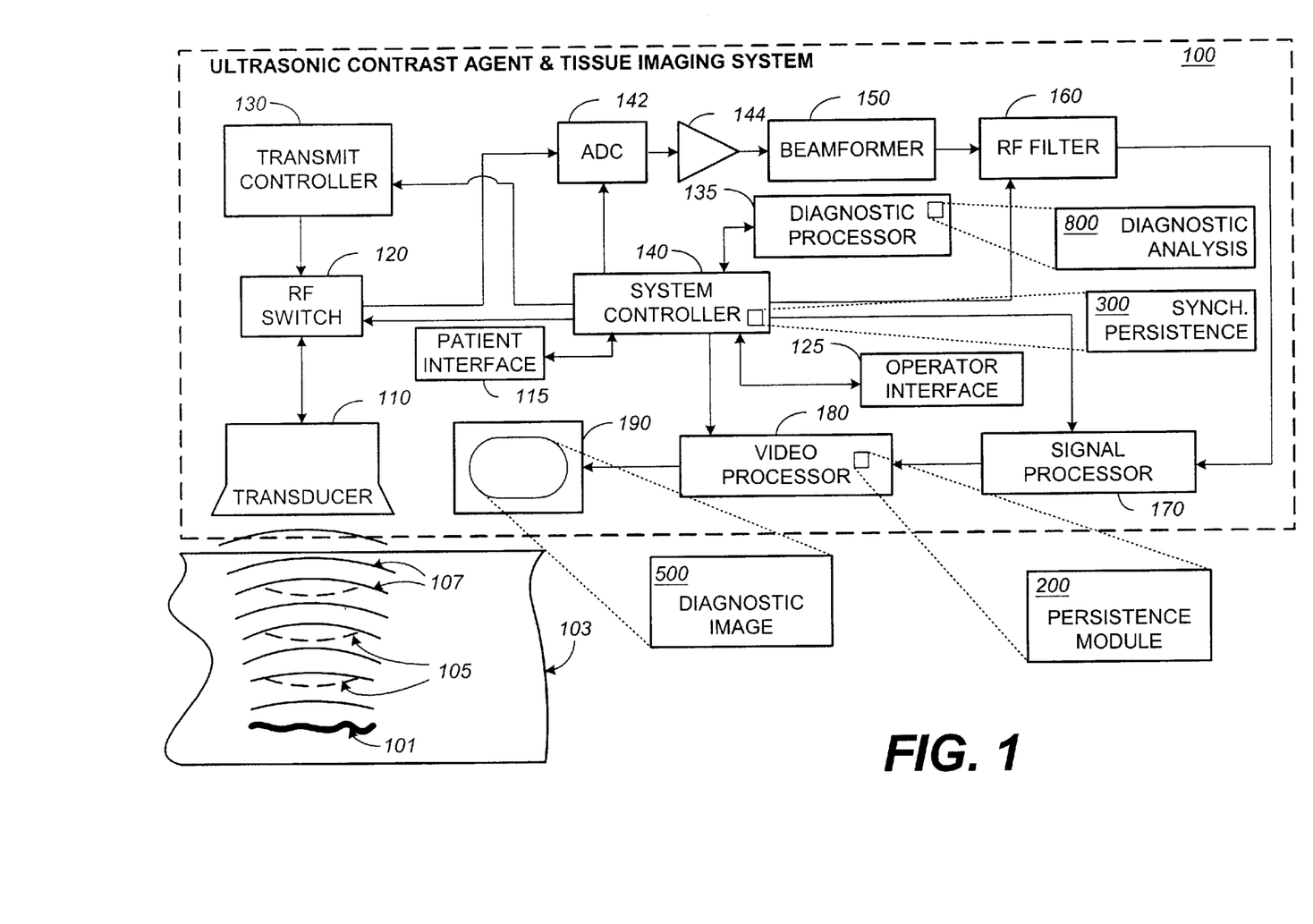
FIG. 1 is a functional block diagram of an ultrasonic imaging system consistent with the teachings of the present invention.

FIG. 1 illustrates a functional block diagram of an ultrasonic imaging system consistent with the teachings and concepts of the present invention. In this regard, an ultrasonic contrast agent and tissue imaging (UCATI) system 100 may comprise a transducer 110, a patient interface 115, a RF switch 120, an operator interface 125, a transmit controller 130, a diagnostic processor 135, a system controller 140, an analog to digital converter (ADC) 142, a time gain control amplifier 144, a beamformer 150, a radio-frequency (RF) filter 160, a signal processor 170, a video processor 180, and a display 190.

As illustrated in FIG. 1, the system controller 140 may be configured to perform a method for synchronized persistence 300. The method for synchronized persistence 300 will be explained in detail in association with the flowchart of FIG. 3. As is also shown in FIG. 1, the video processor 180 may contain a persistence module 200. An exemplary structure and operation of the persistence module 200 will be explained in greater detail with regard to FIG. 2. In accordance with the concepts and teachings of the present invention, the display 190 may generate a plurality of diagnostic ultrasonic images 500, which will be explained in association with FIGS. 5A–5C and FIGS. 6A and 6B. As is further illustrated in FIG. 1, the diagnostic processor 135 may be configured with a method for performing a diagnostic analysis 800, which will be explained in association with the flowchart of FIG. 8.

As shown in FIG. 1, the transducer 110 may be electrically coupled to the RF switch 120. The RF switch 120 may be configured as shown with a transmit input coupled from the transmit controller 130 and a transducer port electrically coupled to the transducer 110. The output of the RF switch 120 may be electrically coupled to an ADC 142 for digital conversion before further processing by the time gain control amplifier 144. The time gain control amplifier 144 may be coupled to a beamformer 150. The beamformer 150 may be coupled to the RF filter 160. The RF filter 160 may be further coupled to a signal processor 170 before further signal processing in the video processor 180. The video processor 180 may then be configured to supply an input signal to the display 190. The system controller 140 may be coupled to the transmit controller 130, the ADC 142, the RF filter 160, and both the signal processor 170 and the video processor 180 to provide necessary timing signals to each of the various devices.

As is also illustrated in the functional block diagram of FIG. 1, the system controller 140 may be communicatively coupled with the patient interface 115 and the operator interface 125. It will be appreciated that the patient interface 115 may provide a number of pertinent parameters to the system controller 140. For example, the patient interface 115 may supply the system controller 140 with data indicative of a patient's breathing cycle, the patient's blood pressure, the patient's heart beat (e.g., electrocardiogram related data), as well as other patient parameters that may be useful in diagnosing a number of patient conditions.

As will be appreciated by those skilled in the art, the system controller 140 may comprise a general-purpose processor, a microprocessor, one or more application-specific integrated circuits (ASICs), a plurality of suitably configured logic gates, and other well known electrical configurations comprised of discrete elements both individually and in various combinations to coordinate the overall operation of the UCATI system 100. Furthermore, the system controller 140, may include one or more computers, memory devices, and other hardware and software components for coordinating the overall operation of the UCATI system 100. In addition, it will be appreciated that the system controller 140 may include software, which comprises an ordered listing of executable instructions for implementing logical functions, which can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. The computer readable medium can be, for instance, an electronic, magnetic, optical, electromagnetic, infrared, or semiconductor system, apparatus, device, or propagation medium.

Similarly, the other processors within the UCATI 100, more specifically, the diagnostic processor 135, the signal processor 170, and the video processor 180, as well as other devices that may be integrated with the UCATI 100 may include one or more general-purpose processors, one or more ASICs, suitably configured logic gates, computers, memory devices, and other like hardware with associated software components for coordinating the overall operation of the particular designated functions associated with the particular processor 135, 170, 180, etc. It will be further appreciated that these processors 135, 170, 180, and other devices may include software modules of their own, which comprise an ordered listing of executable instructions for implementing logical functions that can be embodied in any computer-readable medium.

Having briefly described an exemplary structure for the UCATI 100, a high-level description of the general operation will be presented. In this regard, the RF switch 120 isolates the transmit controller 130 of the UCATI system 100 from the ultrasonic response receiving and processing sections comprising the remaining elements illustrated in FIG. 1. The system architecture illustrated in FIG. 1 provides an electronic transmit signal generated within the transmit controller 130 that is converted to one or more ultrasonic pressure waves wherein illustrated by ultrasound transmit pulses 105. When the ultrasound transmit pulses 105 encounter a tissue layer 103 that is receptive to ultrasound insonification the multiple transmit events or ultrasound transmit pulses 105 penetrate the tissue 103. As long as the magnitude of the multiple ultrasound lines 105 exceeds the attenuation affects of the tissue 103, the multiple ultrasound transmit pulses 105 will reach an internal target 101. Those skilled in the art will appreciate that tissue boundaries or intersections between tissues with different ultrasonic impedances will develop ultrasonic responses at harmonics of the fundamental frequency of the multiple ultrasound lines 105.

As further illustrated in FIG. 1, such harmonic responses may be depicted by ultrasonic reflections 107. It will be further appreciated that tissue 103 insonified with ultrasonic waves develops harmonic responses because the compressional portion of the insonified waveforms travels faster than the rarefactional portions. The different rates of travel of the compressional and the rarefactional portions of a waveform causes the wave to distort producing an harmonic signal which is reflected or scattered back through the various tissue boundaries. It is significant to note that while FIG. 1 illustrates only a second harmonic response to the incident multiple ultrasound transmit pulses 105 impinging the internal target 101 within the tissue 103, other harmonic responses may also observed. As by way of example, it is known that subharmonic, harmonic, and ultraharmonic responses may be created at the tissue boundary between the tissue 103 and the internal target 101. The internal target 101 alone will produce harmonic responses at integer multiples of the fundamental frequency. Various contrast agents on the other hand, have been shown to produce subharmonic, harmonic, and ultraharmonic responses. Hereinafter, subharmonic and ultraharmonic responses may be designated as non-integer harmonic responses less than and greater than a fundamental or transmit frequency, respectively.

Those ultrasonic reflections 107 of a magnitude that exceeds the attenuation effects from traversing tissue layer 103 may be monitored and converted into an electrical signal by the combination of the RF switch 120 and transducer 110. The electrical representation of the ultrasonic reflections 107 may be received at the ADC 142 where they are converted into a digital signal. The time gain control amplifier 144 coupled to the output of the ADC 142 may be configured to adjust amplification in relation to the total time a particular ultrasound reflection 105 needed to traverse the tissue layer 103. In this way, response signals from one or more internal targets 101 will be gain corrected so that ultrasonic reflections 107 generated from relatively shallow objects do not overwhelm (in magnitude) ultrasonic reflections 107 generated from insonified objects further removed from the transducer 110.

The output of the time gain control amplifier 144 may be beamformed, filtered and demodulated via beamformer 150, the RF filter 160, and the signal processor 170. The processed response signal may then be forwarded to the video processor 180. The video version of the response signal may then be forwarded to display 190 where the response signal image may be viewed on a frame by frame basis. As used herein, a frame of data includes any collection of data associated with a plurality of scan lines and any of various coordinate systems.

Other ultrasound systems, including additional or fewer system components or components associated in a different order, may be used. For example, the signal processor 170 may take the form of a B-mode processor, a Doppler processor, or a Doppler processor may be included in a parallel signal-processing path with a B-mode processor. By way of further example, a video recording device or other similar recording device, such as but not limited to, an electrical connection (electronic) having one or more wires, a portable computer diskette (magnetic), a fixed or hard disk drive device (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical) may be associated with the UCATI system 100 to record diagnostic data for post observation evaluation of the data. Note that the computer-readable data storage medium could even be paper or another suitable medium upon which the data is printed, as the data is electronically captured by the UCATI system 100.

In a preferred embodiment, triggering is used to coordinate the acquisition of multiple frames of ultrasonic response information. As illustrated in FIG. 1, the system controller 140 may be configured to coordinate the operation of the transmit controller 130, the RF switch 120, and the various components along the ultrasound signal processing path in order to acquire multiple image frames. In response to a trigger condition, the system controller 140 may cause the acquisition of one or more frames of data. One trigger condition may be derived from information received from an ECG monitor (not shown) in communication with the patient interface 115. In alternative embodiments, the trigger condition may be coordinated with a trigger derived from a patient's breathing cycle, an external timer, or some other trigger indication. Preferably, the trigger condition is selectable by a UCATI system 100 user/operator and monitored by the system controller 140. The selection of one or more trigger inputs may be made via the operator interface 125.

For example, if an ECG trigger is selected, an ECG signal threshold may be set and the output from an ECG associated with the patient interface 115 may be compared to the ECG signal threshold, such as to identify peak systole. One or more thresholds or trigger points throughout a cardiac cycle may be identified as triggering thresholds and compared to the ECG signal. Once a trigger condition is met, the system controller 140 may be configured to coordinate the acquisition and processing of one or more frames of data. It will be appreciated that one or more frames of data may be acquired and processed in response to the same or different trigger conditions.

It will be appreciated that one or more patient parameters may be combined to generate a trigger condition. For example, a patient's peak systole as sensed by an ECG or other similar device may comprise a first trigger input with a peak in a patient's breathing cycle (e.g., a signal derived from a patient exhaling) comprising a second trigger input. In this example, it may prove beneficial to acquire image frames directed at the heart of the patient in response to the combination of a peak systole and an exhale event.

Ultrasound imaging systems such as the UCATI system 100 may be operated in a real-time imaging mode that produces real-time moving images of insonified tissues. These moving images are acquired as discrete static images, but at a high enough frame rate (e.g., 20–30 frames/sec.) to produce the illusion of a continuously moving image. For real time imaging with triggering, multiple frames may be repetitively generated in accordance with one or more ultrasound transmit and triggering scenarios. In these modes, the UCATI system 100 may remain quiescent between acquisition of successive triggered frames, neither transmitting nor receiving. The image display may remain static during quiescent periods, showing the last triggered frame.

In a preferred embodiment the diagnostic processor 135 contains one or more diagnostic algorithms configured to receive various image data from the video processor 180 to generate one or more diagnostic results. As illustrated in FIG. 1, the system controller 140 may provide the signal path for the various image data to the diagnostic processor 135. For example, the diagnostic processor 135 may receive image data via the video processor 180 and operator inputs via the operator interface 125 indicative of a particular blood vessel of interest. Certain image data will provide an indication of the relative position of the vessel's wall as it may appear in a two-dimensional cross-sectional like view. In addition, Doppler mode (i.e., phase shift) information derived from contrast agent laden blood flowing through the vessel and or the blood cells alone may provide an indication of blood flow velocity. Together, the vessel wall measurements and the Doppler information may be used by the diagnostic processor 135 to generate one or more outputs indicative of the relative health of the vessel and the tissues and or organs supplied by the vessel. It will be appreciated that the diagnostic processor 135 may generate one or more signal traces, image displays, data tables, and the like as a means for communicating diagnostic results. It will be further appreciated that the system controller 140 and/or the video processor 180 may be configured to overlay the various diagnostic processor generated results with the ultrasonically processed tissue images.

Figure 2:
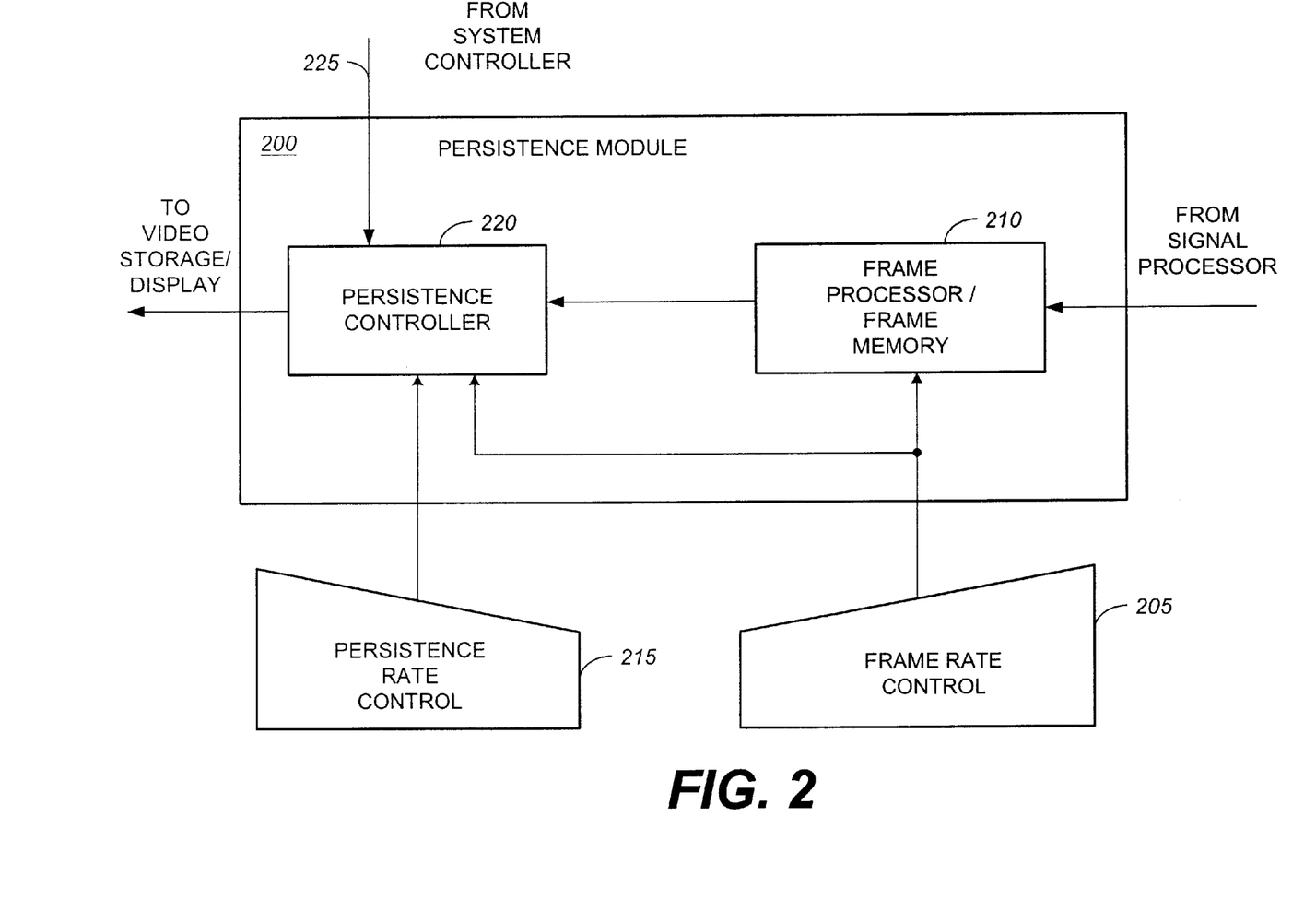
FIG. 2 is a functional block diagram of a persistence module that may be associated with the video processor of FIG. 1.

Having discussed the architecture and operation of the UCATI system 100 in regard to the functional block diagram of FIG. 1, reference is now directed to FIG. 2, which presents a functional block diagram of an exemplary persistence module 200 of FIG. 1. In this regard and as illustrated in FIG. 2, the persistence module 200 may comprise a frame processor/frame memory device 210 and a persistence controller 220. As shown in the block diagram of FIG. 2, the frame processor/frame memory 210 may be configured to receive image-processing data from a signal processor (e.g., the signal processor 170 (FIG. 1). In accordance with a frame-rate control signal 205, which may be provided by the system controller 140 (FIG.1) the frame processor/frame memory 210 may be configured to supply image data to the persistence controller 220. As is also illustrated in FIG. 2, the persistence controller 220 may receive a first input comprising the frame-rate control signal 205 and a second input comprising a persistence rate control input signal 215. It will be appreciated that the frame-rate control input and persistence-rate control input signals 205, 215 may be user selectable via appropriately configured user controls associated with the operator interface 125 (FIG. 1). It will be further appreciated that the frame-rate control input and persistence-rate control input signals 205, 215 may be driven by standard test diagnostic scenarios that may be stored or programmed in a software module residing in or associated with the system controller 140 (FIG. 1).

As shown in FIG. 2, the persistence controller 220 may generate a video storage device/video display input signal in response to the frame data supplied by the frame processor/frame memory 210 and the frame rate control input and persistence rate control input signals 205, 215. A persistence actuator input signal 225 is also provided to the persistence controller 220. As shown in FIG. 2, the persistence actuator input signal 225 may be supplied from the system controller 140 (FIG. 1).

In accordance with a preferred embodiment of the present invention, successive frames of signal processed information are applied to the persistence module 200, which performs a suitable temporal filtering of the successive frames on a pixel by pixel basis during those times that the persistence actuator input signal 225 is enabled. Conversely, the persistence module 200 bypasses temporal filtering of the successive frames during those times that the persistence actuator input signal 225 is disabled. In an alternative embodiment, the persistence actuator input signal 225 selects an appropriate temporal filter and/or appropriate temporal filtering scheme in accordance with an operator selected diagnostic scenario. U.S. Pat. No. 5,788,635, "Adaptive Persistence Processing," issued Aug. 4, 1998 to Wright et al. and assigned to Acuson Corporation and incorporated herein entirely by reference discloses a number of prior art systems and methods for temporally filtering an image. It will be appreciated by those skilled in the art that the persistence filters and methods incorporated by reference herein, together with other variants, may be applied by the UCATI system 100 (FIG. 1).

Figure 3:
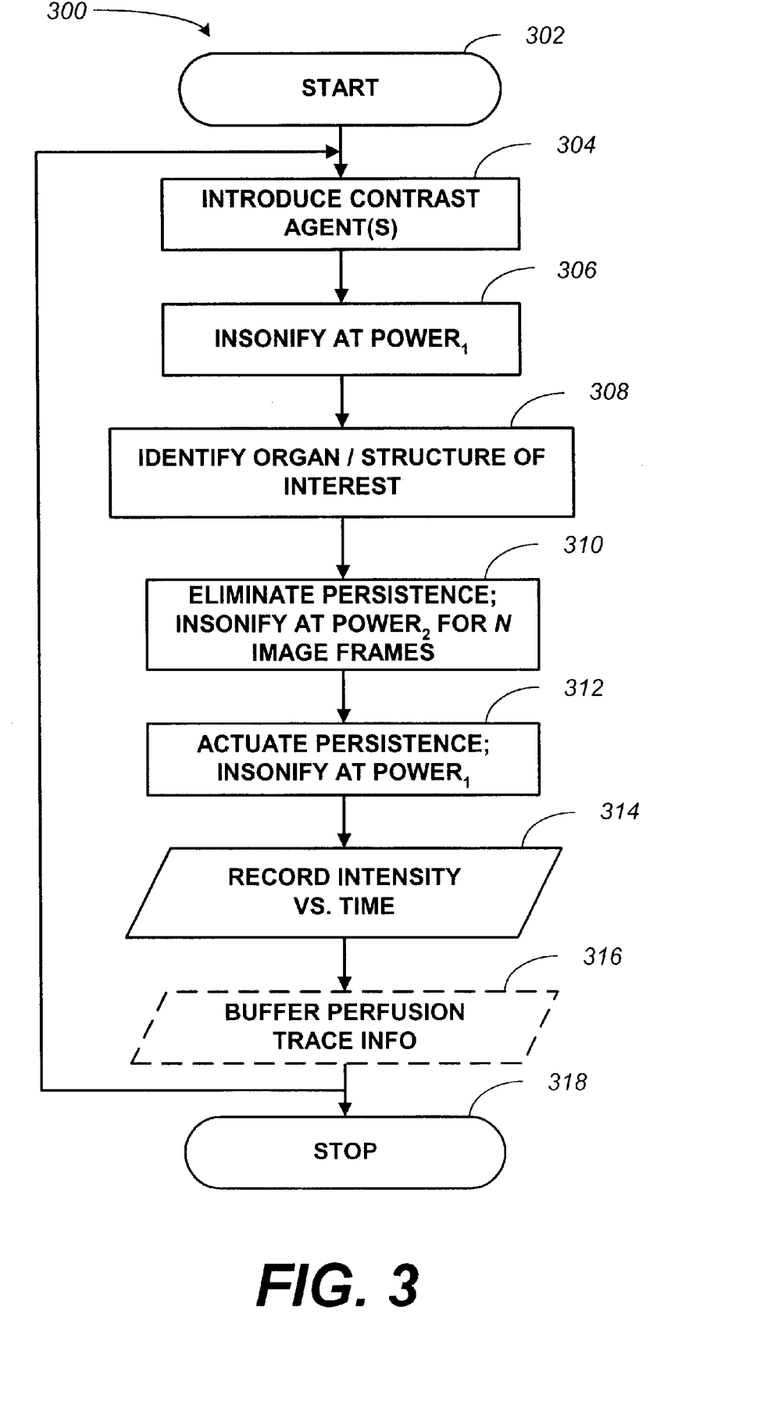
FIG. 3 is a flowchart highlighting a method for contrast agent imaging with synchronized persistence that may be practiced by the ultrasonic imaging system of FIG. 1.

Reference is now directed to the flowchart of FIG. 3, which illustrates a method for synchronized persistence filtering 300 in accordance with a preferred embodiment of the present invention. In this regard, the method for synchronized persistence filtering 300 may begin as shown with step 302, herein labeled, "Start." In step 304 the method for synchronized persistence filtering 300 may introduce one or more ultrasound contrast agents suited for imaging blood flow dynamics or other fluid dynamics within a patient under observation. After the contrast agents have been introduced for a suitable time to permit the contrast agents to flow or perfuse through the particular tissues of interest within a patient, the method for synchronized persistence filtering 300 may perform step 306, where the patient may be insonified with a plurality of ultrasound transmit waves. It will be appreciated that this initial insonification of the tissue or tissues of interest may be performed with a plurality of transmit pulses or waves characterized by parameters suited for imaging of the contrast agent and the surrounding tissues without modifying or destroying the contrast agents.

The method for synchronized persistence filtering 300 may continue to insonify the tissue or tissues of interest to permit the operator to properly orient the patient and the transducer 110 as illustrated in step 308 to identify an organ or structure within an organ that is of interest for further diagnosis and observation. In accordance with the present invention and as illustrated in step 310, the method for synchronized persistence filtering 300 may be configured to eliminate persistence or temporal filtering concurrently with the application of a contrast agent destruction transmit sequence. As is also illustrated in step 310, the method for synchronized persistence filtering 300 may be configured to eliminate persistence filtering and apply the contrast agent destruction sequence for a predetermined number of imaging frames given the present frame processing rate.

Once the predetermined number of frames have been processed by the video controller 190 (FIG. 1) or as indicated by the system controller 140 (FIG. 1), the method for synchronized persistence filtering 300 may proceed by performing step 312, where as illustrated persistence filtering may applied along with a transmit sequence that permits imaging of the contrast agent and the surrounding tissues without modifying or destroying the contrast agents. In accordance with a preferred embodiment, the method for synchronized persistence filtering 300 applies the same transmit sequence that was applied in step 306. It will be appreciated that in alternative embodiments a modified-transmit sequence may be applied. As shown in step 314, the method for synchronized persistence filtering 300 may record contrast agent intensity over time.

Another technique that may be applied by the UCATI system 100 of FIG. 1 to inhibit the inclusion of frames having a high-intensity echo signal resets the contents of the temporal filter in persistence module 200 immediately preceding the first frame after the high-intensity sequence. In this way, the persisted frames contain echo signals only from post high-intensity frames.

Figure 8:
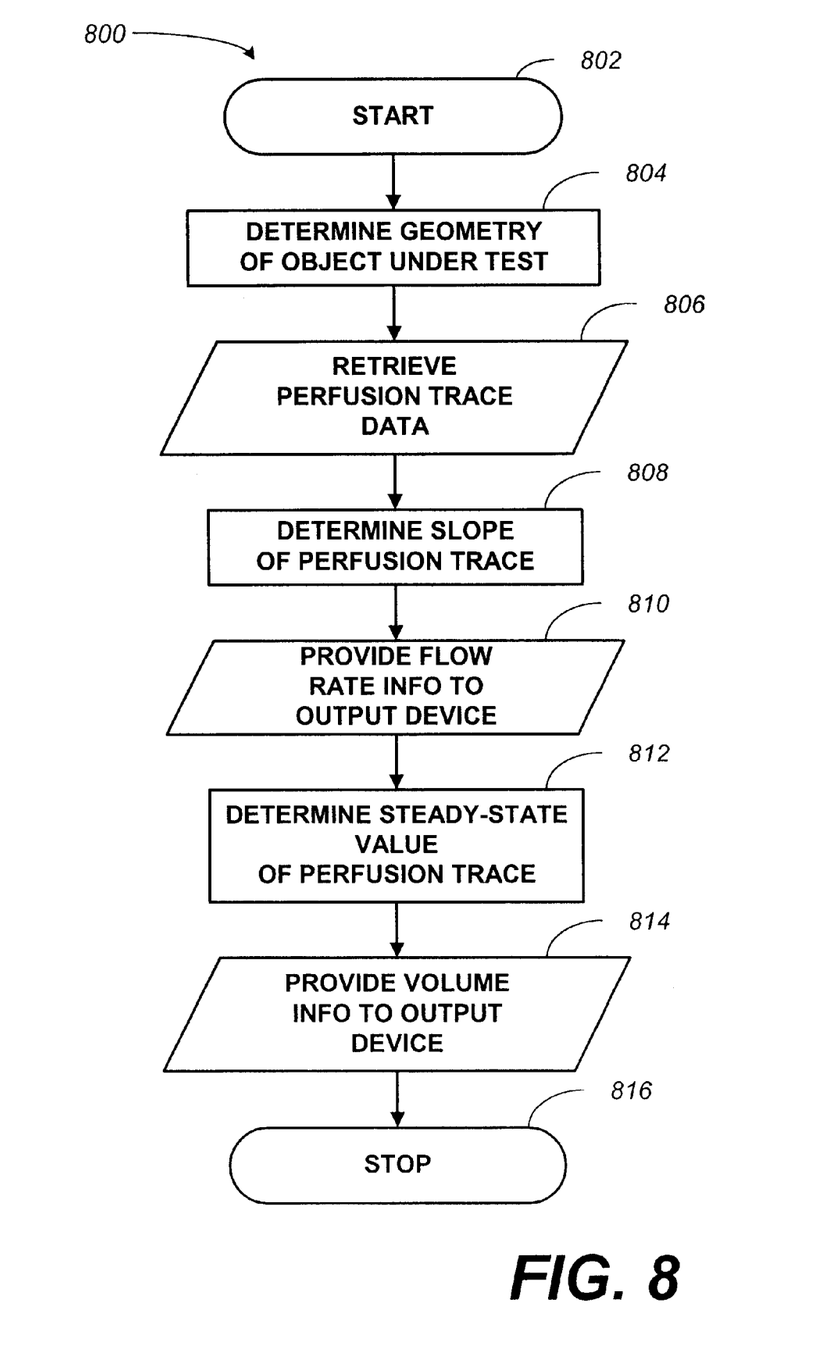
FIG. 8 is a flowchart illustrating a method for performing a blood flow rate and blood volume analysis that may be practiced by the ultrasonic imaging system of FIG. 1.

As will be further explained with regard to the flowchart of FIG. 8, data reflective of contrast agent intensity over time may be combined with data reflective of the surrounding tissue structures to perform one or more diagnostic tests without suffering from the adverse affects of continuously applying a persistence filtering scheme to the image data. As further illustrated in the flowchart of FIG. 3, in an optional step 316, the method for synchronized persistence filtering 300 may buffer a plurality of data points over time reflective of the contrast agent re-perfusion of the tissue or tissues of interest as new unmodified contrast agent traverses the image.

Figure 4A:
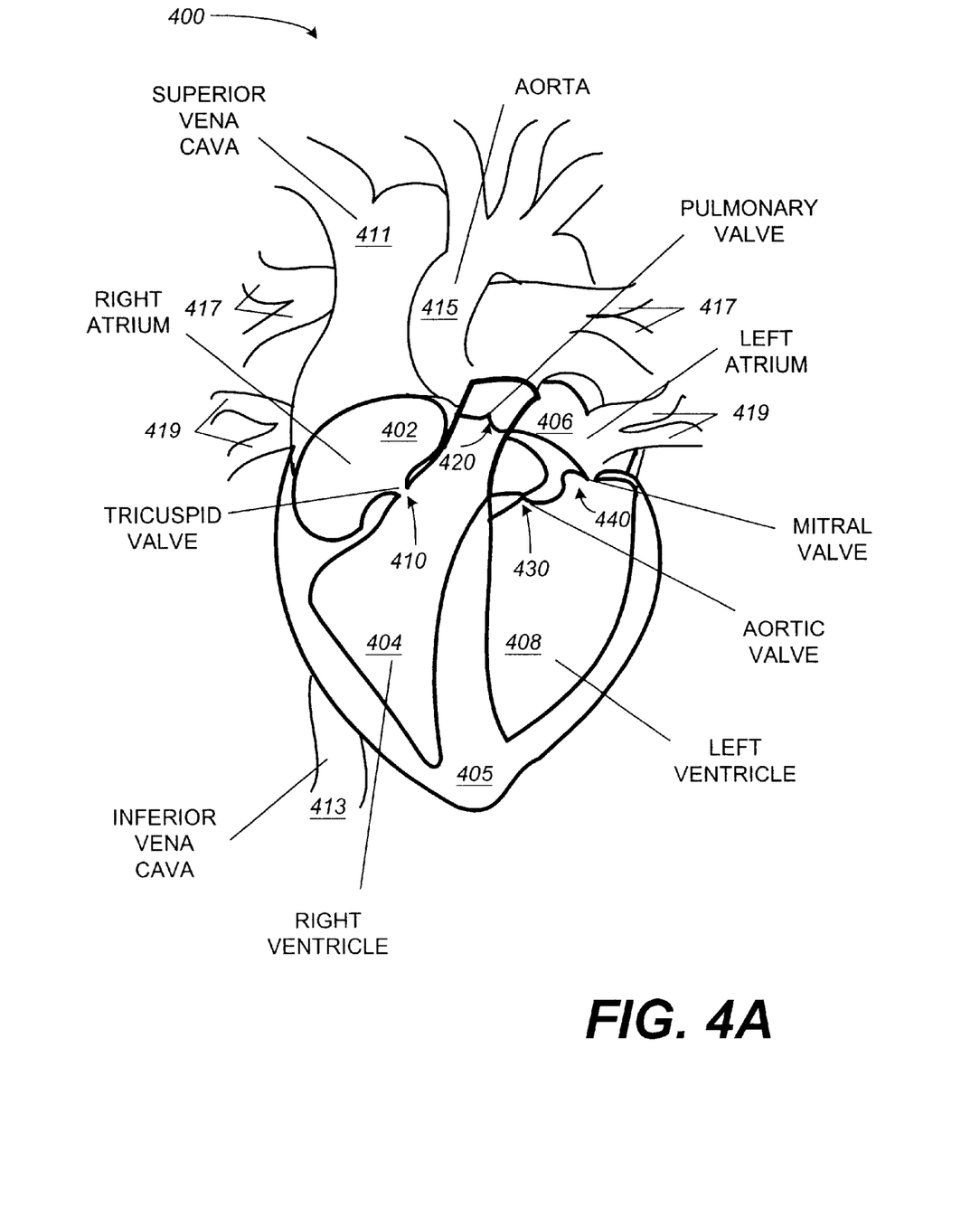
FIGS. 4A and 4B are schematic diagrams illustrating the structure, blood flow, and operation of the human heart, which may be used to initiate the method of FIG. 3.
Figure 4B:
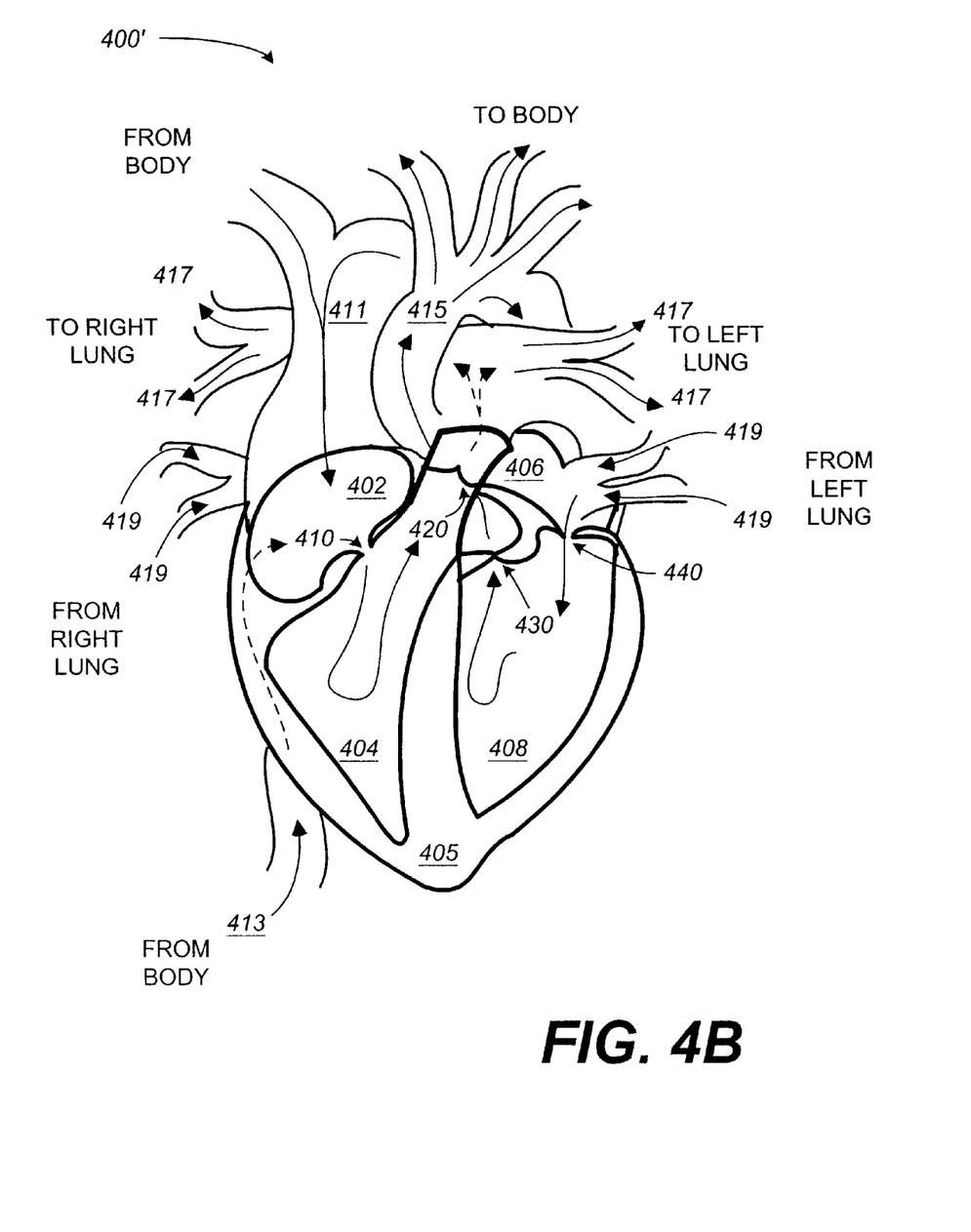

Having described the method for synchronized persistence filtering 300 with regard to the flowchart of FIG. 3, reference is now directed to FIGS. 4A and 4B, which present a cross-sectional view of a human heart that may be observed by the UCATI system 100 of FIG. 1. In this regard, the heart 400 comprises a right and left atrium 402, 406 and a right and left ventricle 404, 408 encompassed by a myocardial tissue layer 405, with a tricuspid valve 410 separating the right atrium 402 from the right ventricle 404 and a mitral valve 440 separating the left atrium 406 from the left ventricle 408. In addition, a pulmonary valve 420 separates the right ventricle 404 from the pulmonary arteries 417 and an aortic valve 430 separates the left ventricle 408 from the aorta 415. As is further illustrated in FIG. 4A, a superior and inferior vena cava 411, 413 return blood from the body to the right atrium 402 and pulmonary veins 419 return blood from the lungs (not shown) to the left atrium 406.

Having described the relative relationships between the various structures and interconnections of the human heart as illustrated in FIG. 4A, reference is now directed to FIG. 4B. In this regard, FIG. 4B illustrates blood flow into, through, and from the heart 400'. As illustrated in FIG. 4B, blood from the body flows into the right atrium 402 via the inferior and the superior vena cava 413, 411 respectively. After the tricuspid valve 410 opens, blood from the right atrium 402 flows past the tricuspid valve 410 into the right ventricle 404. After the pulmonary valve 420 opens, blood in the right ventricle 404 is expelled from the heart and transferred to the right and left lungs (not shown) via the pulmonary arteries 417. After the blood has been oxygenated in the right and left lungs (not shown), the blood is returned via the pulmonary veins 419 to the left atrium 406. After the mitral valve 440 opens, the oxygenated blood flows from the left atrium 406 to the left ventricle 408. Upon opening of the aortic valve 430, blood is expelled from the heart 400' by the left ventricle 408 and is carried by the aorta 415 on its way to the various parts of the body.

When a contrast agent has been introduced into the bloodstream, a significant quantity of the contrast agent will be contained within the right and left atrium 402, 406 respectively, as well as, the right and left ventricles 404, 408 of the heart 400', while only a relatively smaller quantity of contrast agent will enter tissues or organs by way of capillaries within the circulatory system. In this way, the introduction of a contrast agent into the bloodstream followed by ultrasound insonification permits imaging of the blood flow through the heart for a period of time until the contrast agent has perfused the myocardial tissue layer 405.

Figure 5A:
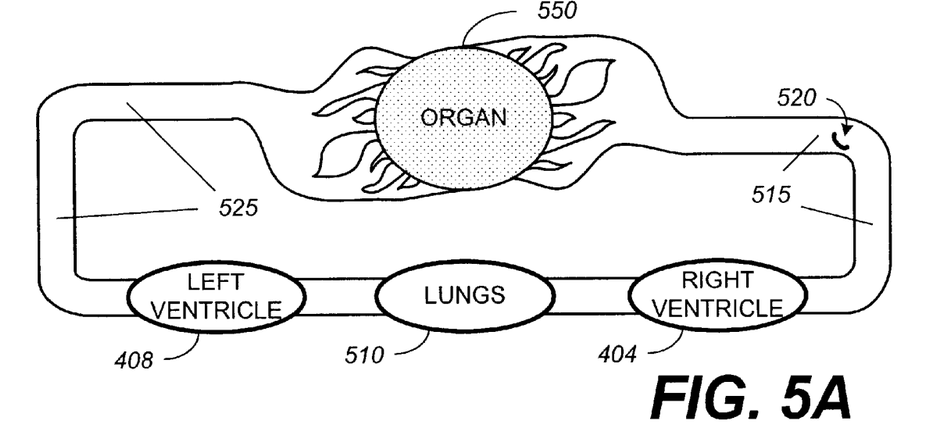
FIGS. 5A–5C illustrate a diagnostic mode applicable to monitor blood flow dynamics through an organ other than the heart of a patient perfused with a contrast agent that may be performed by the ultrasonic imaging system of FIG. 1.
Figure 5B:
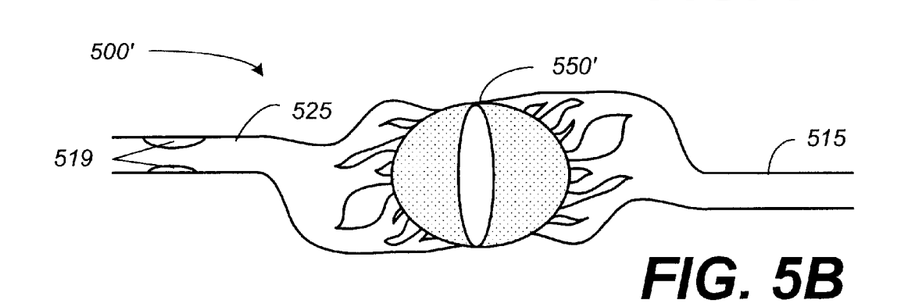
Figure 5C:
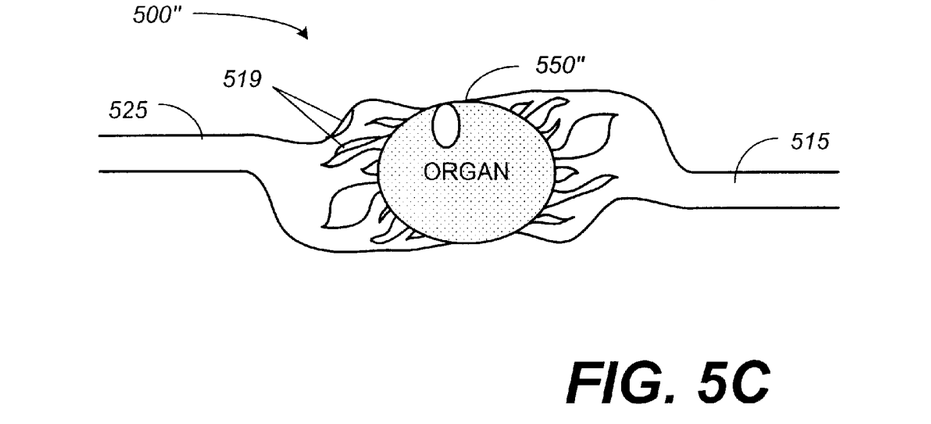

Having described operation of the heart 400, 400' with regard to the illustrations of FIGS. 4A and 4B, reference is now directed to FIGS. 5A through 5C, which illustrate measurement of the rate of perfusion of an organ or area of the body that may be performed by the UCATI system 100 of FIG. 1. In this regard, FIG. 5A illustrates the travel of a contrast agent infused into the bloodstream of a patient via an intravenous injection site 520 through an organ of interest 550. As previously described in relation to FIGS. 4A and 4B, operation of the heart 400, 400' promotes blood circulation from the intravenous injection site 520 in a clockwise direction across the structures illustrated in FIG. 5A. Proceeding in a clockwise fashion from the intravenous injection site 520 located in one of the various veins 515 (one shown for simplicity of illustration), blood traverses the right ventricle 404 on its way to the lungs 510. Blood is returned from the lungs 510 to the heart 400 (not shown in total) where it passes from the left ventricle 408 out to the various parts of the body through the various arteries of the body 525 (one shown for simplicity of illustration). The perfusion rate into the organ of interest 550 can be used to evaluate the viability of blood flow through the organ of interest 550 or to identify the location of a stenosis.

As illustrated in the diagnostic image 500' of FIG. 5B, if a stenosis 519 is located within an artery 525 that supplies blood to organ of interest 550', the rate of expected perfusion across the various capillaries (not shown) of the organ of interest 550' will be reduced across the entire organ of interest 550'. On the other hand, as is illustrated in the exemplary diagnostic image 500" of FIG. 5C, if the stenosis 519 is located within an artery 525 that feeds a portion of the organ of interest 550" the rate of expected perfusion will be reduced across a small portion of the organ of interest 550".

Figure 6A:
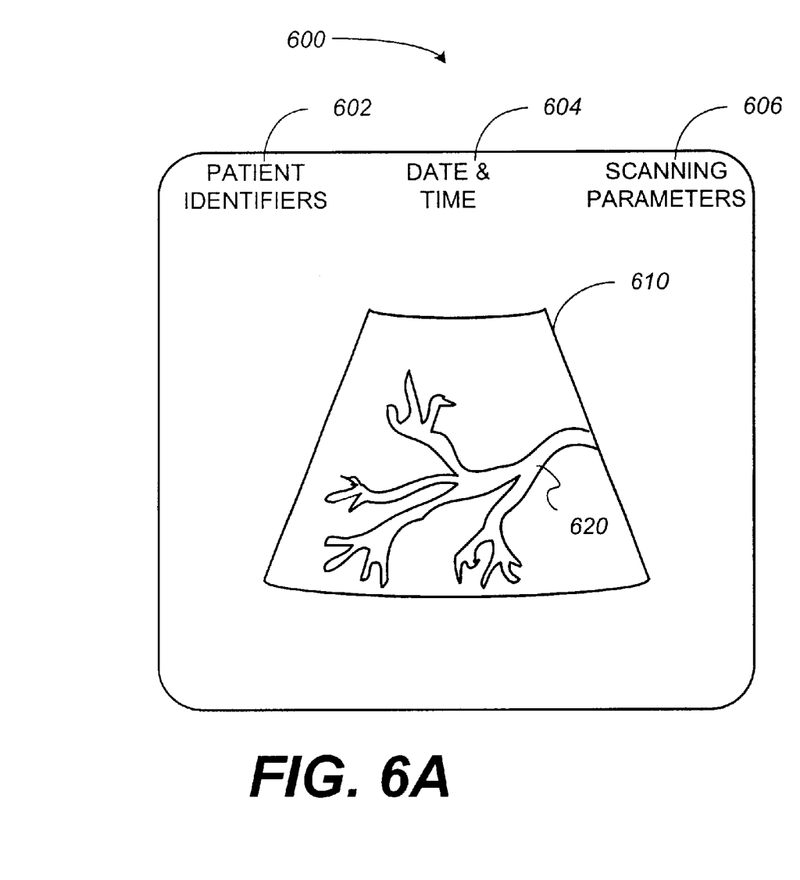
FIGS. 6A and 6B illustrate potential displays that might be generated by the ultrasonic imaging system of FIG. 1, when the image plane is focused on a portion of the circulatory system of a patient.
Figure 6B:
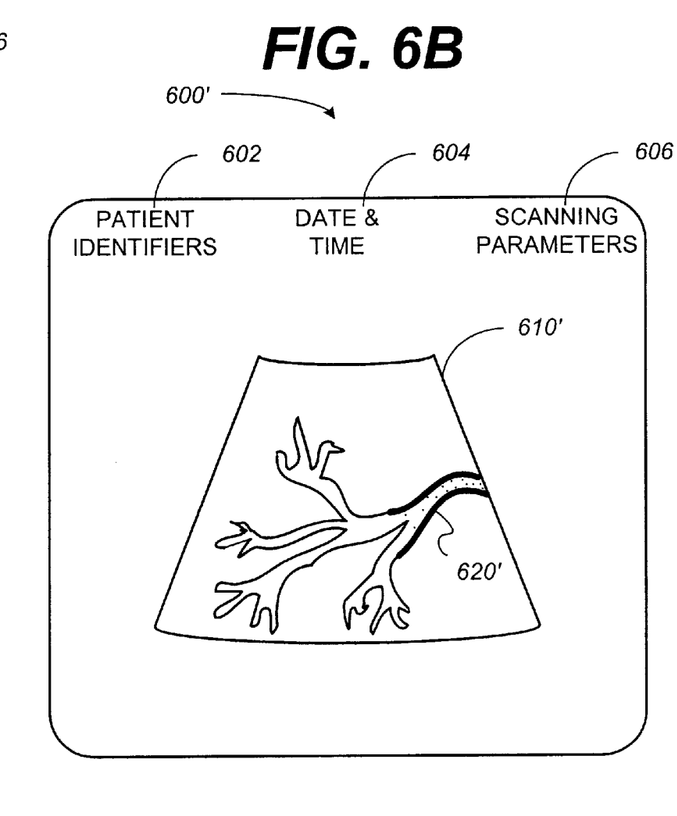

Attention is now directed to FIGS. 6A and 6B, which illustrate potential displays that can be generated from the UCATI system 100 of FIG. 1. In this regard, ultrasound image 600 of FIG. 6A may comprise alphanumeric information in the form of patient identifiers 602, date and time identifiers 604 and scanning parameters 606. In addition to the one or more alphanumeric identifiers, the ultrasound image 600 may comprise a real-time ultrasound image display 610 of a structure in a body such as a portion of the circulatory system 620. A clinical technician may ascertain and locate tissues of interest within an image frame using a real-time image. Preferably the image is created from echoes returned from the non-destructive ultrasonic imaging of one or more contrast agents and/or tissue structures within the patient.

FIG. 6B presents an ultrasound image 600' representing a snapshot of a real-time ultrasound image display 610' of a portion of the circulatory system 620' after introduction of one or more contrast agents in the patient's bloodstream. As illustrated in FIG. 6B the non-linear response from the one or more contrast agents can have a significant effect on the contrast agent to tissue ratio in the ultrasound image 610' showing a portion of the circulatory system 620'. It is important to note that real-time contrast agent images may be acquired at any phase of the heart cycle, not just when the heart is predominately at rest. While the aforementioned real-time imagery of the heart is especially useful in cardiology, variations of this method may prove useful in radiology diagnostics where anatomical structures are more stationary.

Figure 7A:
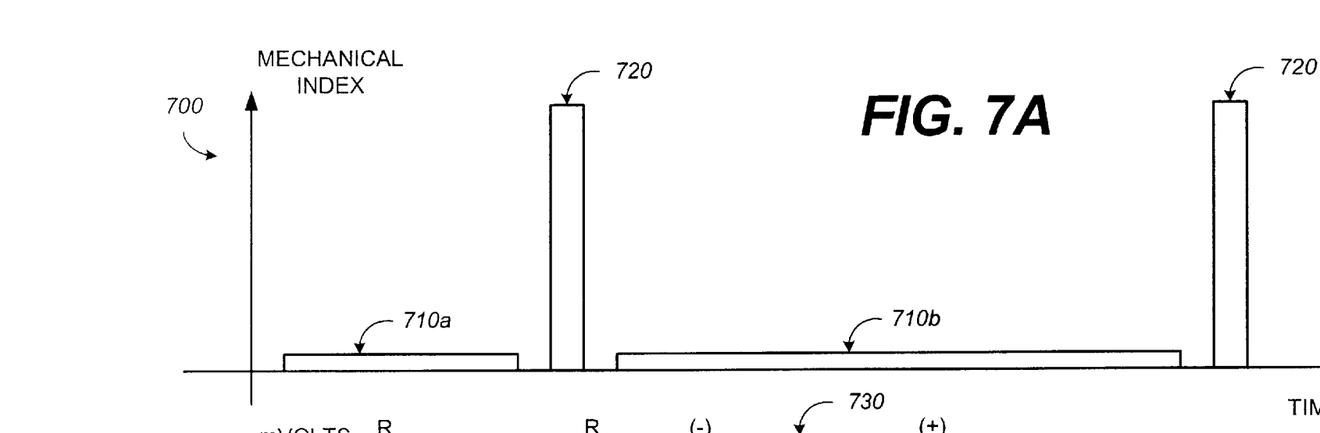
FIG. 7A is a schematic diagram illustrating an exemplary ultrasonic transmit power trace over time that may be produced by the ultrasonic imaging system of FIG. 1.
Figures 7B, 7C:
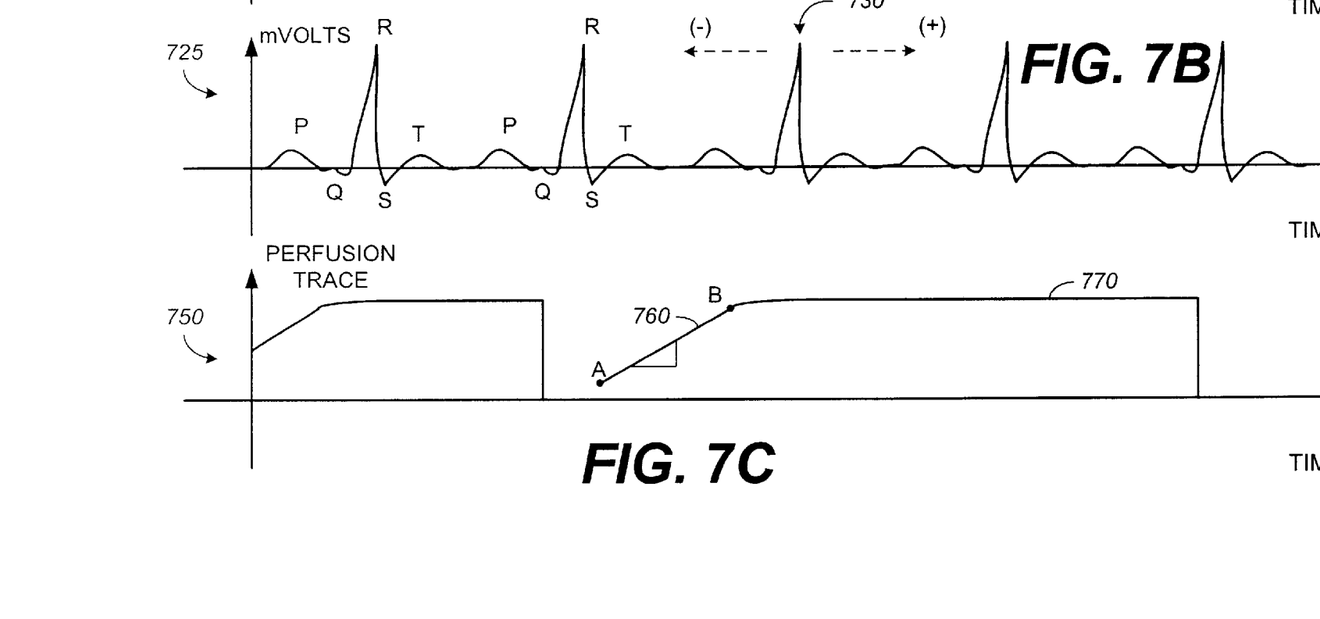
FIG. 7B is a schematic diagram illustrating an exemplary electrocardiogram signal trace that may be provided by the patient interface of FIG. 1.
FIG. 7C is a schematic diagram illustrating a perfusion trace over time that may be generated and stored by the ultrasonic imaging system of FIG. 1 practicing a preferred embodiment of the method illustrated in FIG. 3.

Having generally described the structure and operation of a human heart with regard to blood flow in FIGS. 4A and 4B and generally described how perfusion of a contrast agent in other organs of the body may be performed with regard to FIGS. 5A–5C and observed via the UCATI system 100 of FIG. 1 with regard to the diagnostic images described in FIGS. 6A and 6B, reference is now directed to the timing diagrams of FIGS. 7A–7C, which further illustrate the present invention. In this regard, reference is directed to FIG. 7A which illustrates an exemplary ultrasonic transmit power trace over time that may be generated by the transmit controller 130 under the direction of the system controller 140 of the UCATI system 100 of FIG. 1. As illustrated, an ultrasonic transmit power trace 700 may comprise a first transmit portion 710*a* characterized by a plurality of individual ultrasonic transmit pulses 105 (FIG. 1) having a relatively low mechanical index (MI) and a second portion 720 characterized by a plurality of individual ultrasonic pulses 105 (FIG. 1) having a relatively high MI. In accordance with the teachings and concepts of the present invention, a relatively low MI may vary with regard to the contrast agent or agents selected for introduction into the patient. During this first transmit portion 710*a*, it is desirable to transmit at a MI that results in a relatively stable (i.e., non-destructive) response from a substantial portion of the contrast agent imaged. During the second transmit portion 720, it is desirable to destroy the contrast agent present in the region of interest to enable observation of blood flow parameters over time as contrast agent rich blood re-perfuses the region of interest.

It is significant to note that the second transmit portion 720 representing the application of a destructive transmit sequence may be operator initiated after an operator has identified that a particular region of interest is receiving a sufficient amount of contrast agent over time to adequately image the circulatory structures. It is further significant to note that once the operator has selected a mode characterized by the repetitive application of an ultrasonic transmit destruction sequence, the ultrasonic transmit power trace 700 may be coordinated (e.g., adjusted in time, frequency, and/or in MI) by the system controller 140 and other various components of the UCATI system 100 (FIG. 1) such that a re-perfusion study over time is optimized.

For example, the exemplary electrocardiogram signal trace 725 illustrated in FIG. 7B may be used to provide a triggering input to the system controller 140. In accordance with the teachings and concepts of the present invention, the system controller 140 may be configured to respond to one or more portions of the ECG trace (e.g., the P, Q, R, S and T waves) and or other patient parameters as previously described. As further illustrated in the timing schematic of FIG. 7B, the relative positioning of the ECG trace and or any other exemplary triggering input, for that matter, may be adjusted with respect to the ultrasonic transmit power trace 700.

Importantly, the ultrasonic transmit power trace 700 in accordance with the present invention may be configured in such a manner that it provides a sufficiently long ultrasonic observation period (e.g., the first transmit portion 710*a*) that follows a contrast agent destructive sequence (e.g., the second transmit portion 720) such that the structure under observation reaches a steady-state intensity of contrast agent perfusion over time. This relationship is illustrated in the perfusion trace 750 illustrated in FIG. 7C. As illustrated in FIG. 7C, within a relatively short period of time (e.g., several image frames) after a contrast agent destructive sequence, contrast agent rich blood begins to replace the blood containing the destroyed contrast agent. As illustrated in FIG. 7C, the average or total intensity of the contrast agent re-perfusing the region under observation increases with longer periods between destructive sequences. The slope of the intensity over time as indicated by line segment AB 760 for time segments shorter than that associated with the onset of the maximum intensity contrast agent intensity is an estimate of the velocity of the contrast agent in the tissues under observation. A mathematical combination of the contrast agent velocity and the area of the structure under observation may be used to generate a measure of blood flow volume. In accordance with a preferred embodiment of the present invention, the average flow rate and the average volume may be stored and or applied to various diagnosis algorithms to determine a patient's relative health status.

Having generally described the relative timing between an exemplary ultrasonic transmit power trace 700, an exemplary patient related triggering input (e.g., the ECG trace 725) and the re-perfusion trace 750 with regard to the timing schematics of FIGS. 7A–7C, reference is now directed to FIG. 8, which further illustrates a method for performing a blood flow rate and blood volume analysis that may be practiced by the ultrasonic imaging system of FIG. 1.

Reference is now directed to the flowchart of FIG. 8, which illustrates a method for diagnostic analysis 800 in accordance with a preferred embodiment of the present invention. In this regard, the method for diagnostic analysis 800 may begin as shown with step 802, herein labeled, "Start." In step 804 the method for diagnostic analysis 800 may determine the geometry of an object under test. For example, if a particular artery supplying a portion of the heart muscle is of interest, the method for diagnostic analysis 800 may identify the average distance between the walls of the artery of interest over the image display. It will be appreciated that the distance between the walls may be used to derive both a cross-sectional area over portions of the artery as well as a volumetric measure of the blood which may be supplied by the artery. It will be further appreciated that the blood volume measurement may be coupled with $O_2$ saturation measurements to determine if that particular portion of the heart muscle is receiving a sufficient supply of oxygen over time.

Next, the method for diagnostic analysis 800 may retrieve stored perfusion trace information as indicated in step 806. It will be appreciated that in an alternative embodiment perfusion trace information may be provided and buffered within the diagnostic processor 135 (FIG. 1). As illustrated in step 808, the method for diagnostic analysis 800 may be configured to determine the slope of the perfusion trace to determine the velocity of the contrast agent within the blood in the artery of interest. In accordance with a preferred embodiment, the method for diagnostic analysis 800 is configured to provide the flow rate information to an output device as illustrated in step 810. After having derived a flow rate measurement, the method for diagnostic analysis 800 may be configured to determine a steady-state maximum intensity from the perfusion trace data as indicated in step 812. Next, the method for diagnostic analysis 800 may be configured to provide the volumetric measurement to an output device as illustrated in step 814. Last, the method for diagnostic analysis 800 may terminate as illustrated in step 816, herein labeled, "Stop." It will be appreciated that in alternative embodiments, it may prove useful to repetitively perform the flow rate and blood volume measurements (i.e., repeat steps 806 through 814) to derive more accurate measurements over time. For example the flow rate and blood volume measurements may be buffered in a suitable memory device. The buffered data may then be mathematically combined over a suitable time period.

While particular embodiments of the invention have been disclosed in detail in the foregoing description and drawings for purposes of example, it will be understood by those skilled in the art that variations and modifications thereof can be made without departing from the spirit and scope of the invention as set forth in the following claims.

Having thus described the invention, what is claimed is the following:

1. A method for observing an ultrasonic response of a contrast agent comprising:
   introducing at least one contrast agent into tissue targeted for imaging;
   insonifying tissue with a transducer excited by a first ultrasound-transmit signal suited to peimit real-time observation of contrast agent perfused tissue;
   modifying at least one ultrasonic-transmit signal parameter to generate a second ultrasound-transmit signal wherein a substantial portion of the contrast agent present within the insonified tissue is destroyed; and
   actuating a persistence filter in response to the second ultrasonic-tranismit signal wherein successive image frames acquired after the second ultrasonic-transmit signal is applied are not compromised by persistence filtered results.

2. The method of claim 1, further comprising:
   reapplying the first ultrasound-transmit signal to permit real-time observation of contrast agent re-perfusion through the tissue targeted for imaging; and
   actuating the persistence filter in response to the reapplication of the first ultrasound-transmit signal.

3. The method of claim 1, wherein the first ultrasound-transmit signal comprises a mechanical index (MI) selected wherein the at least one contrast agent introduced in the tissue is substantially unaltered over time.

4. The method of claim 1, wherein the first ultra-sound-transmit signal comprises a frequency above approximately 1.5 MHz.

5. The method of claim 1, wherein the second ultrasound-transmit signal comprises a mechanical index (MI) selected wherein the at least one contrast agent introduced in the tissue is substantially destroyed over time.

6. The method of claim 1, wherein the second ultrasound-transmit signal comprises a frequency below approximately 1.5 MHz.

7. The method of claim 1, wherein the step of modifying is performed in response to a trigger signal.

8. The method of claim 1, wherein the step of actuating comprises disabling the persistence filter.

9. The method of claim 1, wherein the step of actuating comprises resetting the persistence filter.

10. The method of claim 2, wherein the step of actuating comprises enabling the persistence filter.

11. The method of claim 7, wherein the trigger signal is generated in response to at least one patient derived parameter.

12. The method of claim 11, wherein the at least one patient derived parameter is an electrocardiogram waveform.

13. In a method for diagnosing blood flow through a vessel of interest wherein at least one contrast agent has been introduced into the blood and wherein at least one set of ultrasonic image frames are analyzed over time to observe the re-perfusion of the at least one contrast agent within the vessel of interest, the improvement comprising:
   synchronously actuating a persistence filter in response to an environmental condition that results in a substantial increase in the magnitude of a detected ultrasonic signal reflected from the at least one contrast agent within the blood wherein successive image frames acquired after the environmental condition has been removed are not compromised by the persistence filter.

14. The method of claim 13, further comprising:
   estimating the rate of blood flow through the vessel of interest in response to the rate of re-perfusion of the at least one contrast agent through the vessel of interest.

15. The method of claim 13, further comprising:
   estimating the blood volume in a vessel of interest in response to a contrast agent maximum intensity and a measure of the distance between the internal surfaces of the vessel as displayed.

16. The method of claim 15, further comprising:
   estimating the available oxygen to those portions of tissue supplied by the vessel of interest in response to a patient blood oxygen saturation level.

17. An ultrasonic imaging system for harmonic imaging of at least one contrast agent and tissue in a patient, the system comprising:
   means for insonifying a contrast agent perfused tissue of interest with a plurality of ultrasonic pulses wherein the at least one contrast agent can be observed over time;

means for controllably modifying at least one ultrasonic transmit pulse wherein the at least one contrast agent is modified such that the at least one contrast agent can no longer be observed in the tissue of interest; and means for removing the residual effects of a persistence filter from an ultrasound response processing path in response to the modifying means wherein persistence filtering is not applied during a period substantially co-existing with the application of the modified at least one ultrasonic transmit pulse.

18. The system of claim 17, wherein the means for removing is replaced by means for bypassing a persistence filter from an ultrasound response processing path in response to the modifying means wherein persistence filtering is not applied during a period substantially co-existing with the application of the modified at least one ultrasonic transmit pulse.

19. The system of claim 17, wherein the means for removing comprises replacing data associated with a first image frame with data associated with a successive image frame.

20. The system of claim 17, wherein the means for removing comprises replacing data associated with a first image frame with data associated with an immediately preceding image Frame.

21. The system of claim 17, further comprising:
means for diagnosing at least one blood flow parameter.

22. The system of claim 21, wherein the diagnosing means comprises monitoring the re-perfusion of the at least one contrast agent in the tissue of the patient.

23. An ultrasonic diagnostic imaging system for harmonic imaging of at least one contrast agent and tissue in a patient, the system comprising:

a frame memory which temporarily stores a plurality of image frames;

a frame processor coupled to the frame memory wherein the frame processor is configured to generate an output containing image data on a pixel basis;

a persistence actuator responsive to at least one ultrasound transmit signal; and a persistence controller configured to receive the frame processor output wherein the persistence controller mathematically combines image data on a pixel basis from successive image frames in response to the persistence actuator, wherein the persistence actuator disables the persistence controller in response to the at least one ultrasound transmit signal when the transmit signal is configured such that it will substantially destroy the at least one contrast agent in the tissue.

24. The system of claim 23, wherein the persistence actuator disables the persistence controller for a predetermined number of image frames.

25. The system of claim 23, wherein the persistence actuator resets the persistence controller for a predetermined number of image frames.

* * * * *